(12) United States Patent
Nakamura et al.

(10) Patent No.: US 9,463,185 B2
(45) Date of Patent: Oct. 11, 2016

(54) PHARMACEUTICAL CONTAINING PPAR-DELTA AGONIST

(71) Applicants: Nippon Chemiphar Co., Ltd., Tokyo (JP); SENJU PHARMACEUTICAL CO., LTD., Osaka (JP)

(72) Inventors: Yoshikuni Nakamura, Hyogo (JP); Ikuko Hanano, Hyogo (JP); Jun Inoue, Woodland Hills, CA (US)

(73) Assignees: SENJU PHARMACEUTICAL CO., LTD., Osaka (JP); NIPPON CHEMIPHAR CO., LTD., Tokyo (JP)

(*) Notice: Subject to any disclaimer, the term of this patent is extended or adjusted under 35 U.S.C. 154(b) by 0 days.

(21) Appl. No.: 14/317,145

(22) Filed: Jun. 27, 2014

(65) Prior Publication Data

US 2014/0343109 A1  Nov. 20, 2014

Related U.S. Application Data

(62) Division of application No. 12/451,564, filed as application No. PCT/JP2008/059236 on May 20, 2008, now Pat. No. 8,802,705.

(30) Foreign Application Priority Data

May 21, 2007 (JP) ................. 2007-134183

(51) Int. Cl.
| | | |
|---|---|---|
| *A61K 31/421* | (2006.01) | |
| *A61K 31/427* | (2006.01) | |
| *A61K 31/426* | (2006.01) | |
| *C07D 263/32* | (2006.01) | |
| *C07D 277/24* | (2006.01) | |
| *C07D 417/06* | (2006.01) | |

(52) U.S. Cl.
CPC ........... *A61K 31/427* (2013.01); *A61K 31/421* (2013.01); *A61K 31/426* (2013.01); *C07D 263/32* (2013.01); *C07D 277/24* (2013.01); *C07D 417/06* (2013.01)

(58) Field of Classification Search
CPC . A61K 31/421; A61K 31/426; A61K 31/427
See application file for complete search history.

(56) References Cited

U.S. PATENT DOCUMENTS

| | | | |
|---|---|---|---|
| 5,688,765 | A | 11/1997 | Sullivan |
| 2002/0111373 | A1 | 8/2002 | Fujita et al. |
| 2005/0054674 | A1 | 3/2005 | Sakuma et al. |
| 2005/0096363 | A1 | 5/2005 | Sakuma et al. |
| 2007/0060628 | A1 | 3/2007 | Nakamura |
| 2008/0075787 | A1 | 3/2008 | Hibino |
| 2009/0306111 | A1 | 12/2009 | Nakamura et al. |

FOREIGN PATENT DOCUMENTS

| | | |
|---|---|---|
| EP | 0 831 868 | 4/1998 |
| EP | 1 180 519 | 2/2002 |
| EP | 1 424 330 | 6/2004 |
| EP | 1 445 258 | 8/2004 |
| EP | 1 679 074 | 7/2006 |
| EP | 1 964 575 | 9/2008 |
| JP | 2001-039976 | 2/2001 |
| JP | 2002-539166 | 11/2002 |
| JP | 2005-8570 | 1/2005 |
| JP | 2006-176499 | 7/2006 |
| WO | 98/25598 | 6/1998 |
| WO | 02/069994 | 9/2002 |
| WO | 02/076177 | 10/2002 |
| WO | 03/016291 | 2/2003 |
| WO | 03/033493 | 4/2003 |
| WO | 2005/039574 | 5/2005 |
| WO | 2007/061094 | 5/2007 |

OTHER PUBLICATIONS

International Search Report issued Jun. 24, 2008 in International (PCT) Application No. PCT/JP2008/059236.
T. M. Willson et al., "The PPARs: From Orphan Receptors to Drug Discovery", Journal of Medicinal Chemistry, vol. 43, No. 4, pp. 527-550, Feb. 24, 2000.
A. Bonazzi et al., "Regulation of Cyclooxygenase-2 by Hypoxia and Peroxisome Proliferators in the Corneal Epithelium", The Journal of Biological Chemistry, vol. 275, No. 4, pp. 2837-2844, Jan. 28, 2000.
M. J. Kim et al., "Limited Cooperation between Peroxisome Proliferator-Activated Receptors and Retinoid X Receptor Agonists in Sebocyte Growth and Development", Molecular Genetics and Metabolism, vol. 74, pp. 362-369, 2001.
N. S. Tan et al., "Peroxisome Proliferator-Activated Receptor (PPAR)-β as a Target for Wound Healing Drugs", Am. J. Clin. Dermatol., vol. 4, No. 8, pp. 523-530, 2003.
C. Beauregard et al., "Peroxisome Proliferator-Activated Receptor Agonists Inhibit Interleukin-1β-Mediated Nitric Oxide Production in Cultured Lacrimal Gland Acinar Cells", Journal of Ocular Pharmacology and Therapeutics, vol. 19, No. 6, pp. 579-587, 2003.

*Primary Examiner* — Zohreh Fay
(74) *Attorney, Agent, or Firm* — Wenderoth, Lind & Ponack, L.L.P.

(57) ABSTRACT

A preparation containing [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof as an active ingredient is used as an agent for promoting proliferation of meibomian gland epithelial cells or corneal epithelial cells, as well as a therapeutic agent for ocular diseases such as meibomian gland dysfunction, dry eye and the like.

4 Claims, 1 Drawing Sheet human corneal epithelial cell 
rabbit corneal epithelial cell 
monkey meibomian gland epithelial cell 
α    δ/β    γ    GAPDH
PPAR

PHARMACEUTICAL CONTAINING PPAR-DELTA AGONIST

TECHNICAL FIELD

The present invention relates to an agent for promoting proliferation of meibomian gland epithelial cells or corneal epithelial cells, which contains a PPAR (Peroxisome Proliferator-Activated Receptor) δ agonist as an active ingredient.

BACKGROUND ART

A meibomian gland is lipid-producing gland enclosed in both the upper and lower eyelids (palpebra), and secretes a lipid through an opening situated on a conjunctiva side from eyelashes of eyelids. A lipid layer constituting a tear fluid contains a lipid supplied from the meibomian glands as a component, and prevents the tear fluid from evaporating from an eye surface. It is known that patients with meibomian gland dysfunction or meibomitis develop hyperevaporative dry eye, keratoconjunctiva epithelial disorder, corneal epithelial erosion and corneal ulcer, which are associated with dry eye, and the like, since the meibomian gland shows functional deterioration and secretes a lipid at a lower level.

In addition, the cornea consists of epithelium and an external limiting membrane (Bowman's membrane), stroma, a internal limiting membrane (Descemet's membrane) and endothelium. Since the cornea is located at the frontmost part of the eyeball, it is susceptible to external environmental influence, as a result of which various disorders are developed. Examples of the diseases associated with wound or defect of corneal epithelial cells include dry eye syndrome, corneal ulcer, superficial punctuate keratitis, corneal epithelial erosion, ocular allergic diseases associated with corneal lesion such as vernal conjunctivitis, atopic keratoconjunctivitis etc., and the like.

On the other hand, PPAR is one kind of intranuclear receptors expressed in most vertebrates, and is considered to be a transcription factor group closely related to the intracellular sugar or lipid metabolism and cell differentiation. As the subtype, α, δ and γ-types are known. PPARδ is sometimes indicated as PPARβ (non-patent document 1).

As for the distribution of PPAR in the ocular tissue, expression of PPARα and β in the corneal epithelial cells of rabbit is known (non-patent document 2).

There have been reported that 5-[4-(6-methoxy-1-methyl-1H-benzimidazol-2-ylmethoxy)benzyl]thiazolidine-2,4-dione considered to mainly have a PPARγ activation action can be utilized as a therapeutic agent for keratoconjunctival disorders (patent documents 1 and 2), and PPARα, δ or γ agonist is administered for the treatment of ocular diseases (conjunctivitis, dry eye syndrome, keratitis etc.) (patent document 3). In addition, it is known that PPARα is distributed in the liver, kidney and the like, and acts on lipid metabolism and transportation. Furthermore, it has also been reported that an agonist thereof can be utilized as a therapeutic agent for corneal diseases (patent document 4). PPARδ agonists have been reported to promote proliferation and differentiation of rat sebaceous gland epithelial cells (non-patent document 3) and promote wound healing of the skin (non-patent document 4). Besides the above, a method of stimulating proliferation of β-cell by administering a non-thiazolidinedione PPAR ligand and a GLP-1 derivative (patent document 5), inhibition of proliferation of leukemia cell, prostate cancer cell and the like by pioglitazone (PPARγ agonist) (patent document 6) and the like are known.

However, many aspects of the expression and function of PPARα, δ or γ in each animal species and each tissue or cell are yet to be clarified, and whether a PPARδ agonist is useful for ocular diseases in human is not correctly known.

patent document 1: WO2005/039574
patent document 2: JP-A-2001-39976
patent document 3: WO2002/076177
patent document 4: JP-A-2005-008570
patent document 5: WO2002/69994
patent document 6: WO1998/25598
non-patent document 1: J Med Chem 2000, 43: 527-550
non-patent document 2: J Biol Chem 2000, 275: 2837
non-patent document 3: Molecular Genetic and Metabolism 2001, 74: 362-369
non-patent document 4: Am J Clin Dermatol 2003, 4(8): 523-530

DISCLOSURE OF THE INVENTION

Problems to be Solved by the Invention

An object of the present invention is to provide a medicament capable of promoting proliferation of meibomian gland epithelial cells and corneal epithelial cells, which can be a fundamental treatment of ocular diseases such as dry eye and the like, and a therapeutic agent which uses the promoter for ocular diseases such as meibomian gland dysfunction, corneal epithelial disorder, dry eye and the like.

Means of Solving the Problems

The present inventors have conducted intensive studies in view of the above-mentioned problems and found that a specific PPARδ agonist shows a superior action in promoting proliferation of meibomian gland epithelial cells and corneal epithelial cells, which resulted in the completion of the present invention.

Accordingly, the present invention includes at least the following aspects.

(1) An agent for promoting proliferation of a meibomian gland epithelial cell, comprising [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof.

(2) An agent for promoting proliferation of a corneal epithelial cell, comprising [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable is salt thereof.

(3) An agent for treating meibomian gland dysfunction, comprising [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof.

(4) An agent for treating a corneal epithelial disorder, comprising [3-[2-[4-isopropyl-2-(4-trifluoromethyl)phenyl-5-thiazolyl]ethyl]-5-methyl-1,2-benzisoxazol-6-yl]
oxyacetic acid, [4-[3-[2-(4-trifluoromethyl)phenyl-4-isopropyl-5-thiazolyl]propionyl]-2-methylphenoxy]acetic
acid or [4-[3-[2-(2-hydroxy-4-chlorophenyl)-5-isopropyl-4-oxazolyl]propionyl]-2-methylphenoxy]acetic acid, or a
pharmacologically acceptable salt thereof.

(5) An agent for treating dry eye, comprising [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof.

(6) The agent of the aforementioned (5), wherein the dry eye is hyperevaporative dry eye.

(7) Use of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[(3-[2-(2-hydroxy-4-chlorophenyl)-5-isopropyl-4-oxazolyl]propionyl]-2-methylphenoxy]acetic acid, or a pharmacologically acceptable salt thereof, for the production of an agent for promoting proliferation of a meibomian gland epithelial cell.

(8) Use of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof, for the production of an agent for promoting proliferation of a corneal epithelial cell.

(9) Use of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof, for the production of an agent for treating meibomian gland dysfunction.

(10) Use of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]2-methylphenoxy]acetic acid, or a pharmacologically acceptable salt thereof, for the production of an agent for treating a corneal epithelial disorder.

(11) Use of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof, for the production of an agent for treating dry eye.

(12) The use of the aforementioned (11), wherein the dry eye is hyperevaporative dry eye.

(13) A method of promoting proliferation of a meibomian gland epithelial cell, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy] acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of promotion of proliferation of a meibomian gland epithelial cell.

(14) A method of promoting proliferation of a corneal epithelial cell, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of promotion of proliferation of a corneal epithelial cell.

(15) A method of treating meibomian gland dysfunction, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of treatment of meibomian gland dysfunction.

(16) A method of treating a corneal epithelial disorder, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of treatment of a corneal epithelial disorder.

(17) A method of treating dry eye, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of treatment of dry eye.

(18) The method of the aforementioned (17), wherein the dry eye is hyperevaporative dry eye.

Effect of the Invention

The present invention provides a novel meibomian gland epithelial cell proliferative promoter or a corneal epithelial cell proliferative promoter, which promotes proliferation of meibomian gland epithelial cells or corneal epithelial cells. In addition, the therapeutic agent of the present invention can be effectively used for the treatment or improvement of diseases, for example, meibomian gland dysfunction, a corneal epithelial disorder, dry eye and the like.

BRIEF DESCRIPTION OF THE DRAWINGS

FIG. 1 shows the expression of mRNA of PPARα, δ and γ in cultured human corneal epithelial cells (upper panel), cultured rabbit corneal epithelial cells (middle panel), and cultured monkey meibomian gland epithelial cells (lower panel).

BEST MODE FOR CARRYING OUT THE INVENTION

The present invention provides an agent for promoting proliferation of a meibomian gland epithelial cell, comprising [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof (hereinafter sometimes to be collectively referred to as "the compound of the present invention") as an active ingredient. The agent promotes proliferation of meibomian gland epithelial cells. In addition, the present invention provides an agent for promoting proliferation of a corneal epithelial cell, comprising [3-[2-[4-isopropyl-2-(4-trifluoromethyl)phenyl-5-thiazolyl]ethyl]-5-methyl-1,2-benzisoxazol-6-yl]oxyacetic acid, [4-[(3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof as an active ingredient. The agent promotes proliferation of corneal epithelial cells. The cell proliferative promoter in the present invention means both an agent having an action to promote cell division to increase the number of cells, and an agent having an action to suppress cell death to increase the number of cells.

3-[2-[4-Isopropyl-2-(4-trifluoromethyl)phenyl-5-thiazolyl]ethyl]-5-methyl-1,2-benzisoxazol-6-yl]oxyacetic acid (CAS No. 515138-06-4)

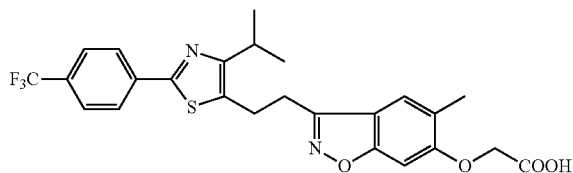 [SMILES: Cc1cc2c(CCc3sc(-c4ccc(C(F)(F)F)cc4)nc3C(C)C)noc2cc1OCC(=O)O]

contained in the promoter of the present invention as an active ingredient is a compound having a PPARδ agonist activity and described in WO2003/033493 (particularly Example 5).

[4-[3-[2-(4-Trifluoromethyl)phenyl-4-isopropyl-5-thiazolyl]propionyl]-2-methylphenoxy]acetic acid (CAS No. 500581-25-8)

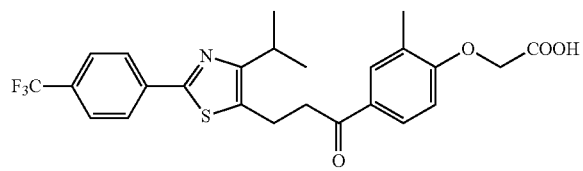 [SMILES: Cc1cc(C(=O)CCc2sc(-c3ccc(C(F)(F)F)cc3)nc2C(C)C)ccc1OCC(=O)O]

contained in the promoter of the present invention as an active ingredient is a compound having a PPARδ agonist activity and described in WO2003/016291 (particularly Example 3).

[4-[3-[2-(2-Hydroxy-4-chlorophenyl)-5-isopropyl-4-oxazolyl]propionyl]-2-methylphenoxy]acetic acid (CAS No. 500581-27-1)

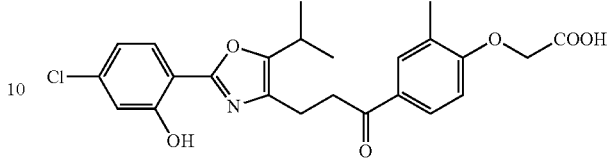

contained in the promoter of the present invention as an active ingredient is a compound having a PPARδ agonist activity and described in WO2003/016291 (particularly Example 6).

Examples of the pharmacologically acceptable salts of these compounds include metal salts with alkali metals such as sodium, potassium etc.; alkaline earth metals such as calcium, magnesium etc.; and the like. In addition, the compound of the present invention also includes a solvate thereof.

The PPARδ agonist in the present invention is a substance that binds to a ligand binding domain (LBD) of PPARδ, activates the receptor, and regulates the transcription of a PPAR target gene. The PPARδ agonist activity can be measured by a yeast two-hybrid method using a chimeric receptor of LBD and GAL4 of yeast, and a reporter gene, in order to exclude influence of other nuclear receptors inherently present in mammalian cells. Specific examples of the measurement method include PPAR-GAL4 assays described in the reference documents, T. M. Willson et al., Journal of Medicinal Chemistry, 2000, vol. 43, No. 4, p. 528-550 and J. M. Lehmann et al., The Journal of Biological Chemistry, 1995, vol. 270, No. 22, p. 12953-12956. The compound of the present invention has been confirmed to have a PPARδ agonist activity according to the methods described in WO2003/033493, Example 12 and WO2003/016291, Example 51.

The compound of the present invention can be synthesized according to the descriptions of WO2003/033493 (particularly Example 5) and WO2003/016291 (particularly Examples 3, 6).

In the promoter of the present invention, the content of the active ingredient is generally 0.000001-1 wt %, preferably 0.00001-1 wt %, most preferably 0.0001-0.1 wt %.

The promoter of the present invention can contain any carrier in addition to the above-mentioned active ingredients. Examples of such carrier include solvents (e.g., water, alcohol etc.), buffers (e.g., phosphate buffer, acetate buffer, borate buffer, carbonate buffer, citrate buffer, Tris buffer, glutamic acid, epsilon aminocaproic acid etc.), preservatives (e.g., benzalkonium chloride, benzethonium chloride, chlorhexidine gluconate, chlorobutanol, benzyl alcohol, sodium dehydroacetate, esters of paraoxybenzoic acid, sodium edetate, boric acid etc.), isotonicity agents (e.g., sodium chloride, potassium chloride, glycerol, mannitol, sorbitol, boric acid, glucose, propylene glycol etc.) and the like.

The promoter of the present invention can be used in vivo or in vitro as a medicament or test reagent and the like.

When the promoter of the present invention is used as a test reagent, it can be utilized as a test reagent in the fields of physiology and biochemistry and in various embodiments.

When the promoter of the present invention is used as a medicament, it is useful as a therapeutic agent for a disease associated with injury or atrophy of meibomian gland epithelial cells, and a disease caused by hypofunction of meibomian gland epithelial cells, since the agent promotes proliferation of meibomian gland epithelial cells. Examples of the diseases include meibomian gland dysfunction, meibomianitis and the like. Furthermore, since the meibomian gland epithelial cells secrete a lipid component in a tear fluid, and the lipid prevents evaporation of the tear fluid and stabilizes the tear fluid layer, the therapeutic agent of the present invention is useful for a disease associated with lipid abnormality (decreased secretion, change of component) in the tear fluid. Examples of the disease include hyperevaporative dry eye.

Moreover, the promoter of the present invention is also useful as a therapeutic agent for a disease associated with injury of corneal epithelial cells (that is, wound or defect), since it promotes proliferation of corneal epithelial cells. The promoter of the present invention is useful as a therapeutic agent for corneal epithelial disorders, specifically, those associated with endogenous diseases such as Sjogren's syndrome, Stevens-Johnson syndrome, keratoconjunctivitis sicca (dry eye) and the like; those associated with exogenous diseases such as post-operation, drug use, trauma, corneal ulcer, meibomianitis, exogenous diseases during wearing contact lenses and the like; those associated with ocular allergic diseases accompanying corneal lesion such as vernal conjunctivitis, atopic keratoconjunctivitis and the like. The promoter of the present invention is also useful for the treatment of superficial punctuate keratitis and corneal epithelial erosion. Furthermore, the promoter of the present invention is also useful as a corneal wound healing promoter.

Furthermore, the promoter of the present invention is useful as an agent for treating dry eye, particularly, highly useful as an agent for treating hyperevaporative dry eye, since the agent simultaneously shows a promoting action on proliferation of corneal epithelial cells and a meibomian gland epithelial cell proliferative action and affords an effect by directly acting on the corneal tissues and an effect of improving the tear fluid function by acting on meibomian gland cells.

In the therapeutic agent of the present invention, the content of the active ingredient is generally 0.000001-1 wt %, preferably 0.00001-1 wt %, most preferably 0.0001-0.1 wt %.

Examples of the subject of administration of the promoter or therapeutic agent of the present invention include mammals (e.g., human, mouse, rat, hamster, rabbit, cat, dog, bovine, sheep, monkey etc.)

The therapeutic agent of the present invention can be used in a dosage form of, for example, eye drop, patch, ointment, lotion, cream, oral agent and the like, and can contain, in addition to the above-mentioned active ingredients, any carrier, for example, a pharmaceutically acceptable carrier.

While the administration route of the therapeutic agent of the present invention is not particularly limited as long as the aforementioned treatment effect is afforded, it is preferably topically administered to the eye. Examples of the dosage form of a topical administration to the eye include eye drop and ophthalmic ointment.

For example, when the therapeutic agent of the present invention is used as an eye drop or ophthalmic ointment, stabilizers (e.g., sodium bisulfite, sodium thiosulfate, sodium edetate, sodium citrate, ascorbic acid, dibutylhydroxytoluene etc.), solubilizing agents (e.g., glycerol, propylene glycol, macrogol, polyoxyethylene hydrogenated castor oil etc.), suspending agents (e.g., polyvinylpyrrolidone, hydroxypropylmethylcellulose, hydroxymethylcellulose, sodium carboxymethylcellulose etc.), emulsifiers (e.g., polyvinylpyrrolidone, soybean lecithin, egg-yolk lecithin, polyoxyethylene hydrogenated castor oil, polysorbate 80 etc.), buffers (e.g., phosphate buffer, acetate buffer, borate buffer, carbonate buffer, citrate buffer, Tris buffer, glutamic acid, epsilon aminocaproic acid etc.), viscous agents (e.g., water-soluble cellulose derivative such as methylcellulose, hydroxyethylcellulose, hydroxypropylmethylcellulose, carboxymethylcellulose etc., sodium chondroitin sulfate, sodium hyaluronate, carboxyvinyl polymer, polyvinyl alcohol, polyvinylpyrrolidone, macrogol etc.), preservatives (e.g., benzalkonium chloride, benzethonium chloride, chlorhexidine gluconate, chlorobutanol, benzyl alcohol, sodium dehydroacetate, esters of paraoxybenzoic acid, sodium edetate, boric acid etc.), isotonicity agents (e.g., sodium chloride, potassium chloride, glycerol, mannitol, sorbitol, boric acid, glucose, propylene glycol etc.), pH adjusters (e.g., hydrochloric acid, sodium hydroxide, phosphoric acid, acetic acid etc.), algefacients (e.g., l-menthol, d-camphor, d-borneol, peppermint oil etc.), ointment bases (white petrolatum, purified lanolin, liquid paraffin, vegetable oil (olive oil, camelia oil, peanuts oil etc.) etc.) and the like can be added as additives. While the amount of the additives varies depending on the kind of additive, use and the like, they may be added in such amounts that affords a concentration capable of achieving the object of use of the additive.

When the therapeutic agent of the present invention is used in the form of an eye drop or ophthalmic ointment, the agent can be produced according to a method generally used in the pharmaceutical field and, for example, based on the method described in the Japanese Pharmacopoeia, 14th Edition, Preparation General Rules, section of eye drop and section of ophthalmic ointment.

Examples of the form of an eye drop include aqueous eye drops (aqueous instillation, aqueous suspension instillation, viscose instillation etc.), non-aqueous eye drops (non-aqueous instillation, non-aqueous suspension instillation etc.), emulsion eye drops and the like.

While the pH of the eye drop is appropriately determined according to the form of the eye drop, it is generally within the range of 4-8. When the eye drop is an aqueous instillation, the pH is particularly preferably adjusted to pH 6-8 from the aspect of solubility of the active ingredient.

The eye drop is generally a preparation sterilized by a method such as sterilization by filtration, irradiation sterilization (e.g., electron sterilization, ultraviolet sterilization, gamma sterilization etc.), autoclave sterilization, hot-air sterilization and the like.

When the agent is formulated into an eye drop, the liquid is preferably filled in an instillation container provided with a liquid drip opening having a small diameter that enables control of the drip amount to facilitate instillation into the eye. The material to be used for the container is synthetic resin, glass, cellulose, pulp and the like, and is appropriately selected according to the property and the amount of use of the active ingredient and the base. From the aspects of squeezability and durability, the container is preferably made of a synthetic resin. Specific examples of the material of the synthetic resin include polyethylene resin (e.g., low density polyethylene or high density polyethylene), polypropylene resin, ethylene-propylene copolymer resin, poly (ethylene terephthalate) resin and the like.

Examples of the instillation container include a container wherein a spigot member is fit into a container body, which are independently molded, an integrally-molded container wherein a liquid is tightly sealed simultaneously with the molding of the container (e.g., WO2004/006826) and the like. When an integrally-molded container is employed, the container is superior in the aspects of cost or hygiene, since the container and the liquid are continuously produced. The instillation container may be a unit dose type container which is disposed after each time of use (e.g., JP-A-9-207959). When this container is employed, a preparation without preservatives, which is highly safe to the cornea, can be formulated. In addition, such containers may be adhesion-packed with a UV blocking film. Furthermore, the containers may be colored (brown, green, blue, yellow etc.) to enhance the UV blocking performance.

The present invention provides a method of promoting proliferation of a meibomian gland epithelial cell, comprising administering an effective amount of the compound of the present invention to a subject in need of promotion of proliferation of meibomian gland epithelial cells. The method is desirably performed for the treatment of meibomian gland dysfunction.

In addition, the present invention provides a method of promoting proliferation of a corneal epithelial cell, comprising administering an effective amount of the compound of the present invention to a subject in need of promotion of proliferation of corneal epithelial cells. The method is desirably performed for the treatment of a corneal epithelial disorder.

In addition, the present invention provides a method of treating dry eye, comprising administering an effective amount of the compound of the present invention to patients suffering from dry eye.

The effective amount of the compound of the present invention cannot be defined automatically since it varies depending on the age, body weight and condition of the subject of administration, a treatment object and the like. When the promoter or therapeutic agent of the present invention is administered to human, for example, a solution containing the compound of the present invention at 0.000001-1 wt %, preferably 0.00001-1 wt %, most preferably 0.0001-0.1 wt %, is generally instilled once-eight times a day by 1-2 drops for one eye/instillation, namely, about 50-200 µL per instillation. The amount of the compound contained in a solution having a concentration and a volume within such ranges can be exemplified as an effective amount.

EXAMPLES

The present invention is explained in detail in the following by referring to Experimental Examples, which are not to be construed as limitative.

Experimental Example 1

Effect on increase of cell number of normal human corneal epithelial cells
1. Cells Used
Normal human corneal epithelial cells (KURABO) were used.
2. Preparation Method of Test Substance Solution
As a test substance, [3-[2-[4-isopropyl-2-(4-trifluoromethyl)phenyl-5-thiazolyl]ethyl]-5-methyl-1,2-benzisoxazol-6-yl]oxyacetic acid (hereinafter to be referred to as compound A) was used. Compound A was dissolved in ethanol (Wako Pure Chemical Industries, Ltd.) to a concentration 200-fold of the final concentration in a culture medium, and the solution was stored at −80° C. until immediately before use.

As a cell culture medium for consideration of the cell number-increasing effect by compound A, a culture medium (basal medium) obtained by adding insulin, hydrocortisone and transferrin contained in HCGS growth additive set (KURABO) to EpiLife (KURABO) was used.
3. Test Method
1) Cell Culture and Addition of Compound a
Normal human corneal epithelial cells cryopreserved in liquid nitrogen were thawed and the cell number was counted. The total amount thereof, was transferred to EpiLife added with all of the HCGS growth additive set (insulin, epidermal growth factor mEGF derived from mouse, hydrocortisone, transferrin, bovine brain hypophysis extract) (4 mL, complete medium), and suspended well therein. The cell suspension was seeded on a fibronectin-coated 24 well plate (Becton Dickinson) at a cell number of $2 \times 10^4$ cells/500 µL/well ($1 \times 10^4$ cells/cm$^2$ since bottom area was 2 cm$^2$).

After completion of cell seeding, the culture plate was incubated in an incubator set to 37° C., 5% $CO_2$, 95% air and 100% humidity for 24 hr, and the culture medium was changed to 400 µL of the basal medium (EpiLife added with insulin, hydrocortisone and transferrin from HCGS growth additives).

After 24 hr thereafter, the culture medium was changed to the following culture medium (each 400 µL).
[1] basal medium alone (non-addition group)
[2] basal medium+mEGF (final concentration: 1 ng/mL; positive control group)
[3] basal medium+compound A (final concentration: 0.1 nM, 1 nM, 0.01 µM, 0.1 µM; compound A addition group)

Ethanol (5 µL) was added to 1 mL each of culture media [1] and [2] to uniformly set the ethanol concentration of all culture media to 0.5%.
2) Measurement of Cell Number
After 24 hr from the start of the stimulation with compound A, the culture supernatant was removed from each well, and a basal medium added with 10% Cell Counting Kit-8 (DOJINDO) was dispensed to each well by 200 µL. After dispensing, the culture plate was transferred to an incubator set to 37° C., 5% $CO_2$, 95% air and 100% humidity and incubated for 2 hr. The supernatant (100 µL) was transferred to a 96 well culture plate for tissue culture (Corning), and the absorbance of each well at 450 nm was measured with a microplate reader (Dainippon Sumitomo Pharma Co., Ltd.), and used as an index of cell number increase.
4. Statistical Analysis
The values of the positive control group and the compound A addition group were calculated based on the average absorbance of the non-addition group as 100%, and the non-addition group was compared with the compound A addition group and positive control group according to the Dunnett multiple comparison test (one-tailed). A critical value of less than 5% as a result of the test was judged as significant.
5. Test Results
The cell number increasing effect of each group is shown in Table 1. The measured absorbances show that the cell number of the positive control group and compound A addition group is significantly higher than that of the non-addition group where the cell number of the non-addition group is 100%, and an increase in the cell number is suggested in these groups ($p<0.01$). From the test results, it has been clarified that compound A increases the cell number of normal human corneal epithelial cells.

TABLE 1

| group | Cell number increase rate (%) | significant difference (to non-addition group) |
|---|---|---|
| non-addition group | 100.0 ± 7.7 | |
| mEGF | 147.5 ± 47.2 | ** |
| $10^{-10}$M compound A | 177.4 ± 20.8 | ** |
| $10^{-9}$M compound A | 169.0 ± 8.2 | ** |
| $10^{-8}$M compound A | 187.4 ± 10.2 | ** |
| $10^{-7}$M compound A | 172.6 ± 16.0 | ** |

The changes in the cell number when compound A was added to cultivated normal human corneal epithelial cells are shown in the values relative to the average value of the non-addition group as 100% (mean±standard deviation, N=3-4). ** in the Table shows a significant difference from the non-addition group ($p<0.01$).

Experimental Example 2

Study of Promoting Action on Corneal Epithelial Wound Healing

1. Animal Used

Male Japanese white rabbits (KITAYAMA LABES Co., Ltd.) were used. The experimental animals were used according to the International Guiding Principles for Biomedical Research involving Animals.

2. Preparation Method of Test Substance Installation

Compound A was used as a test substance. Compound A was dissolved in the following vehicle at 0.0005% or suspended in the following vehicle at 0.005% and used as an instillation.

| sodium dihydrogen phosphate dihydrate | 0.05 g |
| sodium chloride | 0.45 g |
| ultra-pure water | e.q. |
| polysorbate 80 | 0.05 mL |
| sodium hydroxide | e.q. |
| total amount | 50 mL (pH 7.0) |

As a control for the compound A administration group, the above-mentioned vehicle instillation group free of medicament was used.

3. Experimental Method

1) Corneal Epithelial Scraping

Animals received intramuscular injection (1 mL/kg) of a Selactal (2% xylazine; Bayer, Ltd.): Ketalar (5% ketamine; DAIICHI SANKYO COMPANY, LIMITED)=1:1 mixture for systemic anesthesia, and oxybuprocaine hydrochloride instillation (Benoxil instillation 0.4%; Santen Pharmaceutical CO., Ltd.) and then the eyeballs were exposed. Using a trephine with a diameter of 10 mm, a mark (diameter 10 mm) was stamped on the corneal epithelium in the central part of the cornea, and the entire corneal epithelial layer within the marked circle was scraped off with a handy rooter under a stereomicroscope. After scraping, the corneal surface was washed with physiological saline (OTSUKA PHARMACEUTICAL FACTORY, INC.), and the corneal epithelial scraping treatment was completed by placing the eyeball back in the orbitae.

2) Administration

Compound A instillation or an instillation vehicle was instilled by 50 μL each time into the treated eye with a micropipette twice a day on the day of corneal epithelial scraping and four times a day from the next day to the completion of the test.

3) Evaluation

Using the time point when the corneal epithelial scraping was completed in all animals as a test starting time (0 hr), the area of corneal epithelium defect was quantified 40, 48, 56 and 64 hr later, based on which wound healing of the corneal epithelium was evaluated. To be precise, 0.1% fluorescein sodium (Wako Pure Chemical Industries, Ltd.) solution (10 μL) was instilled into the treated eye at each time point, and the anterior ocular segment of the animals was immediately photographed using a slit lamp with a blue filter, whereby the fluorescein-stained corneal epithelial deficient region was recorded. The developed photograph was stored as digital images on a computer, and the area of the fluorescein-stained corneal epithelial defect was measured using an image analysis software (Image-Pro Plus).

4. Statistical Analysis

The area of the fluorescein-stained corneal epithelial defect measured at each time point was calculated based on the initial value of each animal as 100%, and taken as the ratio of the remaining corneal epithelial defect. The ratio of the remaining corneal epithelial defect at each time point was compared between the vehicle instillation group and compound A instillation group using the t-test. A critical value of less than 5% as a result of the test was judged as significant.

5. Test Results

The ratio of the remaining corneal epithelial defect in the vehicle instillation group, and 0.0005% and 0.005% compound A instillation groups at each time point of the measurement is shown in Table 2. It is shown that the ratio of the corneal epithelial defect significantly decreased in the 0.005% compound A instillation group in 40 hours from the corneal epithelial scraping. The ratio significantly decreased in the 0.0005% and 0.005% compound A instillation groups 48 hours later. From the test results, it has been clarified that instillation of compound A promotes wound healing of corneal epithelial defect.

TABLE 2

| group | vehicle instillation group (%) | 0.0005% compound A instillation group (%) | 0.005% compound A instillation group (%) |
|---|---|---|---|
| 0 hr (initial value) | 100.0 ± 0.0 | 100.0 ± 0.0 | 100.0 ± 0.0 |
| 40 hr later | 28.1 ± 5.3 | 24.8 ± 2.7 | 18.6 ± 8.0* |
| 48 hr later | 18.1 ± 6.1 | 11.8 ± 2.9* | 9.1 ± 6.4* |
| 56 hr later | 11.1 ± 8.1 | 3.8 ± 2.8 | 3.4 ± 3.7 |
| 64 hr later | 5.1 ± 6.9 | 0.8 ± 1.4 | 0.9 ± 1.3 |

The ratio (%) of the remaining corneal epithelial defect after the corneal epithelial scraping treatment of the rabbit eyes was calculated for each animal based on the initial value as 100% (mean±standard deviation, N=6). * in the Table shows a significant difference from the vehicle instillation group ($p<0.05$).

Experimental Example 3

Effect on Cell Number Increase in Meibomian Gland Epithelial Cells

1. Preparation of Monkey Meibomian Gland Epithelial Cell

An eyelid of monkey isolated and stored in D-PBS was transferred to a clean bench, and cell preparation was aseptically performed as follows.

The isolated eyelid was immersed in 80% ethanol for 30 sec, washed three times with D-PBS added with 1% penicillin-streptomycin (Invitrogen), and transferred to a minimum essential medium (MEM; Invitrogen). The adipose tissue and muscular tissue surrounding the meibomian glandular tissue of the eyelid were removed under a stereomicroscope. They were transferred to MEM containing 0.3 U/ml, collagenase A (Roche Diagnostics) and 2.4 U/mL dispase II (Roche Diagnostics), and shaken at 37° C. for 4 hr and at 4° C. overnight. The enzyme-treated tissue was set under a stereomicroscope, and the eyelash and eyelid connective tissue were removed to isolate the meibomian glandular tissue. Trypsin-EDTA (4 mL, Invitrogen) was added to the isolated glandular tissue, and the mixture was incubated at 37° C. for 10 min. After incubation, MEM (5 mL) containing 10% FBS (Invitrogen) was added thereto to stop the enzyme reaction, and the tissue constituting cells were dispersed by repeated suction and discharge of the mixture 5 times using an injection syringe equipped with a 21 G injection needle. The cell dispersion was passed through 100 μm and 40 μm nylon filters (Cell Strainer; Falcon), and cell mass and the like contained therein which could not be treated with the enzyme were removed. The cell suspension passed through the filters was collected in a centrifuge tube (50 mL) and centrifuged at room temperature, 1,500 rpm for 5 min. To the cell layers containing the object cells obtained by the centrifugation was added 80 μL of D-PBS containing 0.5% bovine serum albumin (BSA; Sigma-Aldrich), and the cells were sufficiently suspended therein. Anti-Fibroblast Microbeads (Militenyi Biotec, 20 μL) was added thereto, and the mixture was left standing at room temperature for 30 min. After completion of the reaction with an antibody, 2 mL of D-PBS containing 0.5% BSA was added thereto, and the mixture was centrifuged again at room temperature, 1,500 rpm for 5 min. To the cell layers containing the object cells obtained by the centrifugation was added 1 mL of D-PBS containing 0.5% BSA, and the cells were sufficiently suspended therein. The suspension was added dropwise to LD column (Militenyi Biotec) equilibrated in advance with a column washing solution (D-PBS containing 2 mM EDTA (DOJINDO LABORATORIES) and 0.5% BSA). Then, 2 mL of the column washing solution was added dropwise to the LD column. During the period of from immediately after dropwise addition of the cell suspension to the completion of the dropwise addition of the column washing solution, the antibody-unlabeled object cells (non-fibroblast) that did not adsorb to the column were recovered in a 50 mL centrifuge tube. The cells collected in the centrifuge tube were centrifuged at room temperature, 1,500 rpm for 5 min, and the supernatant was removed. The sediment was suspended in Defined Keratinocyte Serum Free Medium (5 mL), centrifuged at room temperature, 1,500 rpm for 5 min, and removed the supernatant. Again, the residue was suspended in DK-SFM (3 mL), centrifuged at room temperature and 1,500 rpm for 5 min, and the supernatant was removed. The cells were suspended in DK-SFM (2 mL), and seeded on a 6 well multi-well plate for cell culture, which had been treated with collagen. The seeded cells were cultured in Defined keratinocyte-Serum Free Medium (DK-SFM; Invitrogen, attached Supplement was added as instructed in the preparation protocol), cultured in an incubator (SANYO) set to 37° C., 5% $CO_2$, 95% air, 100% humidity, and the culture medium was exchanged with a new one every 48 hr until the cells became subconfluent.

2. Preparation Method of Test Substance Solution

As a test substance, compound A, [4-[3-[2-(4-trifluoromethyl)phenyl-4-isopropyl-5-thiazolyl]propionyl]-2-methylphenoxy]acetic acid (hereinafter to be referred to as compound B) or [4-[3-[2-(2-hydroxy-4-chlorophenyl)-5-isopropyl-4-oxazolyl]propionyl]-2-methylphenoxy]acetic acid (hereinafter to be referred to as compound C) was used. The test substance was dissolved in ethanol (Nacalai Tesque) to a concentration 200-fold of the final concentration in a culture medium, and the solution was stored at −80° C. until immediately before use.

For consideration of cell proliferation promoting effect by the test substance, a culture medium obtained by removing the supplement attached to DK-SFM from DK-SFM was used as a basal medium (basal DK-SFM). As a positive control for confirmation of the cell proliferation promoting effect, a culture medium (complete DK-SFM) was used, which was obtained by adding the attached supplement to the basal medium.

3. Test Method

1) Collagen Treatment of Culture Plate

The day before using a culture plate, 50 μL of 0.01% type I collagen (Nitta Gelatin Inc.) was dispensed to each well of the culture plate, and allowed to coat the well at 4° C. until immediately before the test. On the day of the test, the type I collagen solution was removed and the bottom of the culture plate was washed three times with D-PBS, and used for the test as a collagen-treated culture plate.

2) Cell Culture and Addition of Test Substance

For the test, monkey meibomian gland epithelial cells were used, which had been cultured to sub-confluent in a culture plate (diameter 3.5 cm) and cryopreserved in liquid nitrogen. The cells suspended in Cellbanker (Nippon Zenyaku Kogyo Co., Ltd.) and cryopreserved were thawed, and transferred to a 50 mL centrifuge tube, and 10-fold amount of complete DK-SFM was added. The cell layers were collected by centrifugation at room temperature, 1,500 rpm for 5 min. A suitable amount of complete DK-SFM was added to a concentration of the obtained cells of $3\times10^6$ cells/mL. The cell suspension was dispensed to each well by 64 μL such that the cell number was $6\times10^4$ cells/cm² per the bottom area (0.32 cm²) of the collagen-treated 96-well culture plate for tissue culture. After completion of the cell seeding, the culture plate was transferred to an incubator set to 37° C., 5% $CO_2$, 95% air, 100% humidity and cultured for 24 hr. The culture medium was exchanged with basal DK-SFM (100 μL) and further cultured for 24 hr. Then, the culture medium in each well of the culture plate was exchanged with 100 μL each of the following culture medium, the culture plate was placed back in the incubator and cell stimulation was started.

[1] basal medium alone (basal DK-SFM, non-addition group)

[2] basal medium+supplement (complete DK-SFM, positive control group)

[3] basal medium+compound A (final concentration: 0.01 μM, 0.1 μM and 1 μM; compound A addition group)

[4] basal medium+compound B (final concentration: 0.01 μM, 0.1 μM and 1 μM; compound B addition group)

[5] basal medium+compound C (final concentration: 0.01 μM, 0.1 μM and 1 μM; compound C addition group)

Ethanol (5 μL) was added to 1 mL each of culture media [1] and [2] to uniformly set the ethanol concentration of all culture media to 0.5%.

2) Measurement of Cell Number

After 48 hr from the first cell stimulation, the culture medium was exchanged with the culture medium of the above-mentioned [1]-[5] prepared anew. After 48 hr, the culture medium was exchanged again with the culture medium of the above-mentioned [1]-[5] prepared anew.

After 48 hr, the culture supernatant was removed from each well, and a basal medium added with 10% Cell Counting Kit-8 (DOJINDO) was dispensed to each well by 100 μL. After dispensing, the culture plate was transferred to an incubator set to 37° C., 5% $CO_2$, 95% air and 100% humidity and incubated for 2 hr. After incubation for 2 hr, the absorbance at 450 nm was measured with a microplate reader (Dainippon Sumitomo Pharma Co., Ltd.), and used as an index of cell number increase.

4. Statistical Analysis

The values of each of the positive control group and the test substance addition group were calculated based on the average absorbance of the non-addition group as 100%, and the non-addition, group was compared with the test substance addition group and positive control group according to the Dunnett multiple comparison test (one-tailed). A critical value of less than 5% as a result of the test was judged as significant.

5. Test Results

The cell number increase promoting effect of each group is shown in Table 3. The measured absorbances show that the increase in the cell number of each test substance addition group is significantly higher than that of the non-addition group where the cell number of the non-addition group is 100%, and an increase in the cell number is suggested. In the positive control group for confirmation of the cell number increase promoting effect, a tendency toward cell number increase was observed, though not significant. From the test results, it has been clarified that each test substance increases the number of monkey meibomian gland epithelial cells.

TABLE 3

| group | cell number increase ratio (%) | significant difference (to non-addition group) |
|---|---|---|
| non-addition group | 100.0 ± 7.1 | |
| supplement | 114.2 ± 6.7 | |
| $10^{-8}$M compound A | 175.3 ± 9.0 | ** |
| $10^{-7}$M compound A | 177.1 ± 9.7 | ** |
| $10^{-6}$M compound A | 189.8 ± 13.1 | ** |
| $10^{-8}$M compound B | 155.0 ± 28.0 | ** |
| $10^{-7}$M compound B | 174.4 ± 8.9 | ** |
| $10^{-6}$M compound B | 158.8 ± 15.2 | ** |
| $10^{-8}$M compound C | 155.0 ± 11.6 | ** |
| $10^{-7}$M compound C | 175.2 ± 7.8 | ** |
| $10^{-6}$M compound C | 179.4 ± 7.5 | ** |

The changes in the cell number when each test substance or supplement (positive control) was added to cultured monkey meibomian gland epithelial cells are shown in values based on the average value of the non-addition group as 100% (mean±standard deviation, N=5 or 10). ** in the Table shows a significant difference from the non-addition group ($p<0.01$).

Experimental Example 4

Effect on Increase of Cell Number of Normal Human Corneal Epithelial Cells

1. Cells used

Normal human corneal epithelial cells (KURABO) were used.

2. Test Substance and Preparation Method

As a test substance, compound B or compound C was used. Compound B and compound C were each dissolved in ethanol (Wako Pure Chemical Industries, Ltd.) to a concentration 200-fold of the final concentration in a culture medium, and the solution was stored at −80° C. until immediately before use.

As a cell culture medium for consideration of the cell number-increasing effect by compound B and compound C, a culture medium (basal medium) obtained by adding insulin, hydrocortisone and transferrin contained in HCGS growth additive set (KURABO) to EpiLife (KURABO) was used.

3. Test Method

1) Cell Culture and Addition of Test Substance

Normal human corneal epithelial cells cryopreserved in liquid nitrogen were thawed and the cell number was counted. The total amount thereof was transferred to EpiLife added with all of the HCGS growth additive set (insulin, epidermal growth factor mEGF derived from mouse, hydrocortisone, transferrin, bovine brain hypophysis extract) (4 mL, complete medium), and suspended well therein. The cell suspension was seeded on a fibronectin-coated 24 well plate (Becton Dickinson) at a cell number of $2 \times 10^4$ cells/500 μL/well ($1 \times 10^4$ cells/cm$^2$ since bottom area was 2 cm$^2$). After completion of cell seeding, the culture plate was incubated in an incubator set to 37° C., 5% $CO_2$, 95% air and 100% humidity for 24 hr, and the culture medium was changed to 400 μL of the basal medium (EpiLife added with insulin, hydrocortisone and transferrin from HCGS growth additives). After 24 hr thereafter, the culture medium was changed to the following culture medium (each 400 μL).

[1] basal medium alone (non-addition group)
[2] basal medium+mEGF (final concentration: 1 ng/mL; positive control group)
[3] basal medium+compound B (final concentration: 0.01 μM, 0.1 μM, 1 μM; compound B addition group)
[4] basal medium+compound C (final concentration: 0.01 μM, 0.1 μM, 1 μM; compound C addition group)

Ethanol (5 μL) was added to 1 mL each of culture media [1] and [2] to uniformly set the ethanol concentration of all culture media to 0.5%.

2) Measurement of Cell Number

After 24 hr from the start of the stimulation with compound B or compound C, the culture supernatant was removed from each well, and a basal medium added with 10% Cell Counting Kit-8 (DOJINDO) was dispensed to each well by 200 μL. After dispensing, the culture plate was transferred to an incubator set to 37° C., 5% $CO_2$, 95% air and 100% humidity and incubated for 2 hr. The supernatant (100 μL) was transferred to a 96 well culture plate for tissue culture (Corning), and the absorbance of each well at 450 nm was measured with a microplate reader (Dainippon Sumitomo Pharma Co., Ltd.), and used as an index of cell number increase.

4. Statistical Analysis

The values of the positive control group and the compound B or compound C addition group were calculated based on the average absorbance of the non-addition group as 100%, and the non-addition group was compared with the compound B or compound C addition group and positive control group according to the Dunnett multiple comparison test (one-tailed). A critical value of less than 5% as a result of the test was judged as significant.

5. Test Results

The cell number increasing effect of each group is shown in Table 4. The measured absorbances show that the cell number of the positive control group, compound B addition group, and compound C addition group is significantly higher than that of the non-addition group where increase in the cell number of the non-addition group is 100%, and an increase in the cell number is suggested in these groups ($p<0.01$). From the test results, it has been clarified that both compound B and compound C increase the cell number of normal human corneal epithelial cells.

TABLE 4

| group | cell number increase rate (%) | significant difference (to non-addition group) |
|---|---|---|
| non-addition group | 100.0 ± 32.2 | |
| mEGF | 232.8 ± 22.5 | ** |
| $10^{-8}$M compound B | 252.4 ± 34.7 | ** |
| $10^{-7}$M compound B | 256.4 ± 11.0 | ** |
| $10^{-6}$M compound B | 254.3 ± 11.7 | ** |
| $10^{-8}$M compound C | 243.3 ± 6.6 | ** |
| $10^{-7}$M compound C | 247.5 ± 14.1 | ** |
| $10^{-6}$M compound C | 260.2 ± 2.5 | ** |

The changes in the cell number when compound B or compound C was added to cultivated normal human corneal epithelial cells are shown in the values relative to the average value of the non-addition group as 100% (mean±standard deviation, N=4). ** in the Table shows a significant difference from the non-addition group ($p<0.01$).

Experimental Example 5

Expression of PPARs in Corneal Epithelial Cell and Meibomian Gland Epithelial Cell 1. Cells Used Monkey meibomian gland epithelial cells used were those prepared and cultured by a method similar to (Experimental Example 3). Human corneal epithelial cells (KURABO) used were those cultured in a incubator set to 37° C., 5% $CO_2$, 95% air, 100% humidity in a serum-free basal medium for normal human corneal epithelial cell proliferation (EpiLife; KURABO). Rabbit corneal epithelial cells used were those prepared and cultured by the following method.

Cornea was cut out from the eyeballs isolated from an euthanized rabbit, stored in Dulbecco's phosphate buffered saline (D-PBS; Invitrogen) and transferred to a clean bench. The following cell preparation operations were all performed aseptically.

The isolated corneal button was washed three times in D-PBS added with 1% penicillin-streptomycin (Invitrogen), and transferred to a minimum essential medium (MEM; Invitrogen). Corneal endothelium cells and Descemet's membrane of the corneal button immersed in MEM were detached with a knife for eye surgery (Alcon), and the detached corneal button (corneal stroma and corneal epithelium) was transferred to MEM added with dispase II (Roche Diagnostics) at 2.4 U/ml. This was incubated at 37° C. for 1 hr, and the corneal button treated with dispase II was transferred to MEM. The corneal epithelium of the corneal button immersed in MEM was detached with a knife for eye surgery, and corneal button residue (corneal stroma) was removed from the MEM. The MEM containing the detached corneal epithelial cells was collected in a 50 mL centrifuge tube, centrifuged at room temperature, 1,500 rpm for 5 min and the supernatant was discarded to give corneal epithelial cell layers. To the corneal epithelial cell layers was added 1 mL of trypsin-EDTA (Invitrogen) and the mixture was mixed well and incubated at 37° C. for 5 min to eliminate cell-cell adhesion. Thereto was added 9 mL of MEM containing 10% fetal bovine serum (FBS; Invitrogen) to stop the enzyme reaction, and the mixture was centrifuged again at room temperature, 1,500 rpm for 5 min to give corneal epithelial cell layers. To the obtained corneal epithelial cell layers was added 1 mL of a serum-free liquid medium for normal rabbit corneal epithelial cell growth (RCGM2; KURABO) to suspend the cells therein, and the cells were seeded in a cell culture plate (diameter 10 cm, IWAKI) added with 9 mL of RCGM2. The seeded cells were cultured in a incubator (SANYO) set to 37° C., 5% $CO_2$, 95% air, 100% humidity. The culture medium was exchanged with a new one every 48 hr until the day of the test.

2. Test Method

1) Extraction of Total RNA from Cell

Total RNA was extracted from each cell according to a conventional method for TRIzol Reagent (Invitrogen).

2) Preparation of cDNA from Extracted Total RNA

The total RNA extracted was treated with DNase at 37° C. for 30 min to remove genomic DNA according to a conventional method for DNA-free (Ambion).

cDNA was prepared from the extracted total RNA according to a conventional method for Superscript II Reverse Transcriptase (Invitrogen). That is, cDNA complementary to the total RNA treated with DNase was prepared from 1 μg of the total RNA using a random primer (Invitrogen).

3) Amplification of PPARs Gene (Polymerase Chain Reaction; PCR)

PCR of PPARs gene was performed according to a conventional method for Platinum PCR SuperMix (Invitrogen). The PPARs primer was designed such that the PCR product became about 200 bps in reference to the known sequences of human, chimpanzee, *Macaca fascicularis*, bovine, mouse and the like.

PPARα:
(SEQ ID NO: 1)
GTAGAATCTGCGGGGACAAG (sense)

(SEQ ID NO: 2)
: GTTGTGTGACATCCCGACAG (antisense)

PPARδ:
(SEQ ID NO: 3)
TTCCTTCCAGCAGCTACACA (sense)

(SEQ ID NO: 4)
: GATCGTACGACGGAAGAAGC (antisense)

PPARγ:
(SEQ ID NO: 5)
CTCCGTGGATCTCTCCGTAA (sense)

(SEQ ID NO: 6)
: GATGCAGGCTCCACTTTGAT (antisense)

The PCR reaction was completed by a reaction at 94° C. for 2 min 15 sec, followed by 35 cycles of 3-step reactions at 94° C. for 30 sec, 55° C. for 30 sec and 72° C. for 30 sec. The sample after PCR reaction was electrophoresed on 2% agarose gel, and DNA separated in the gel was stained with SYBR Gold (Molecular Probes). The images of the stained DNA luminescent on a UV transilluminator were stored as digital data.

3. Test Results

The bands of the DNA after electrophoresis are shown in FIG. 1. As a result of this test, it was confirmed that all of PPARα, PPARδ and PPARγ were expressed in human corneal epithelial cells and monkey meibomian gland epithelial cells. In rabbit corneal epithelial cells, only the expression of PPARδ was confirmed. Bonazzi et al. report that PPARα and PPARβ (=δ) from PPARs are expressed in rabbit corneal epithelial cells (Bonazzi A. et al., J. Biol. Chem. (2000); 275 (4): 2837-2844). In the report, they used a special method to detect PPARα, which suggests that the PPARα expression level in rabbit corneal epithelial cells is extremely small.

INDUSTRIAL APPLICABILITY

According to the present invention, a novel agent for promoting proliferation of meibomian gland epithelial cells or a novel agent for promoting proliferation of corneal epithelial cells is provided, and the agent promotes proliferation of meibomian gland epithelial cells or corneal epithelial cells. In addition, the therapeutic agent of the present invention can be effectively used for the treatment or improvement of diseases such as meibomian gland dysfunction, corneal epithelial disorder, dry eye and the like.

This application is based on a patent application No. 2007-134183 filed in Japan (filing date: May 21, 2007), the contents of which are incorporated in full herein by this reference.

The invention claimed is:

1. A method of promoting proliferation of a meibomian gland epithelial cell, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of promotion of proliferation of a meibomian gland epithelial cell.

2. A method of treating meibomian gland dysfunction, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of treatment of meibomian gland dysfunction.

3. A method of treating dry eye, comprising administering an effective amount of [3-[2-[4-isopropyl-2-(4-trifluoromethyl)phenyl-5-thiazolyl]ethyl]-5-methyl-1,2-benzisoxazol-6-yl]oxyacetic acid, [4-[3-[2-(4-trifluoromethyl)phenyl-4-isopropyl-5-thiazolyl]propionyl]-2-methylphenoxy]acetic acid or [4-[3-[2-(2-hydroxy-4-chlorophenyl)-5-isopropyl-4-oxazolyl]propionyl]-2-methylphenoxy]acetic acid, or a pharmacologically acceptable salt thereof to a subject in need of treatment of dry eye.

4. The method of claim 3, wherein the dry eye is hyper-evaporative dry eye.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 1
gtagaatctg cggggacaag                                                     20

<210> SEQ ID NO 2
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 2
gttgtgtgac atcccgacag                                                     20

<210> SEQ ID NO 3
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 3
ttccttccag cagctacaca                                                     20

<210> SEQ ID NO 4
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 4
gatcgtacga cggaagaagc                                                     20

<210> SEQ ID NO 5
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 5
ctccgtggat ctctccgtaa                                                     20

<210> SEQ ID NO 6
<211> LENGTH: 20
<212> TYPE: DNA
```

```
<213> ORGANISM: Artificial sequence
<220> FEATURE:
<223> OTHER INFORMATION: Synthetic construct; primer

<400> SEQUENCE: 6
gatgcaggct ccactttgat                                             20
```